United States Patent [19]

Castellano et al.

[11] Patent Number: 5,730,723
[45] Date of Patent: Mar. 24, 1998

[54] GAS PRESSURED NEEDLE-LESS INJECTION DEVICE AND METHOD

[75] Inventors: Thomas P. Castellano, Reno, Nev.; Robert Schumecher, Beverly Hills, Calif.

[73] Assignee: Visionary Medical Products Corporation, Inc., Beverly Hills, Calif.

[21] Appl. No.: 719,459

[22] Filed: Sep. 25, 1996

Related U.S. Application Data

[63] Continuation-in-part of Ser. No. 541,470, Oct. 10, 1995, abandoned.

[51] Int. Cl.⁶ .................................................. A61M 5/30
[52] U.S. Cl. ............................ 604/68; 604/70; 604/143
[58] Field of Search ........................ 604/68, 70, 72, 604/110, 143, 146, 148; 222/389

[56] References Cited

U.S. PATENT DOCUMENTS

| | | |
|---|---|---|
| 2,642,062 | 6/1953 | May . |
| 3,507,276 | 4/1970 | Burgess . |
| 3,688,765 | 9/1972 | Gasaway . |
| 4,722,728 | 2/1988 | Dixon . |
| 4,874,367 | 10/1989 | Edwards . |
| 4,941,880 | 7/1990 | Burns . |
| 5,009,637 | 4/1991 | Newman et al. . |
| 5,024,656 | 6/1991 | Gasaway et al. . |
| 5,064,413 | 11/1991 | McKinnon et al. . |

FOREIGN PATENT DOCUMENTS

| | | |
|---|---|---|
| 0295917 | 12/1988 | European Pat. Off. . |
| WO 89/08469 | 9/1989 | WIPO . |
| WO 95/03844 | 2/1995 | WIPO . |
| WO 96/28202 | 9/1996 | WIPO . |

OTHER PUBLICATIONS

PCT International Search Report, Feb. 25, 1997, 5 pages PCT/US 96/16172.

*Primary Examiner*—Michael Powell Buiz
*Assistant Examiner*—Nguyen At
*Attorney, Agent, or Firm*—Loeb & Loeb LLP

[57] ABSTRACT

An improved medication delivery device is a pen sized instrument that is powered by compressed inert gas. The needle-less injector device contains pre-filled and pre-measured medication dosages. The injector device has a pre-filled and self-contained compressed gas for providing pressure to inject the medication into the skin surface without the use of a needle. The injector device has a pressure sensitive deployment mechanism which insures proper seating of the injector face against the skin surface before medication delivery is accomplished. The needle-less injector device assures safe use by inexperienced operators (including children) under adverse conditions.

6 Claims, 3 Drawing Sheets

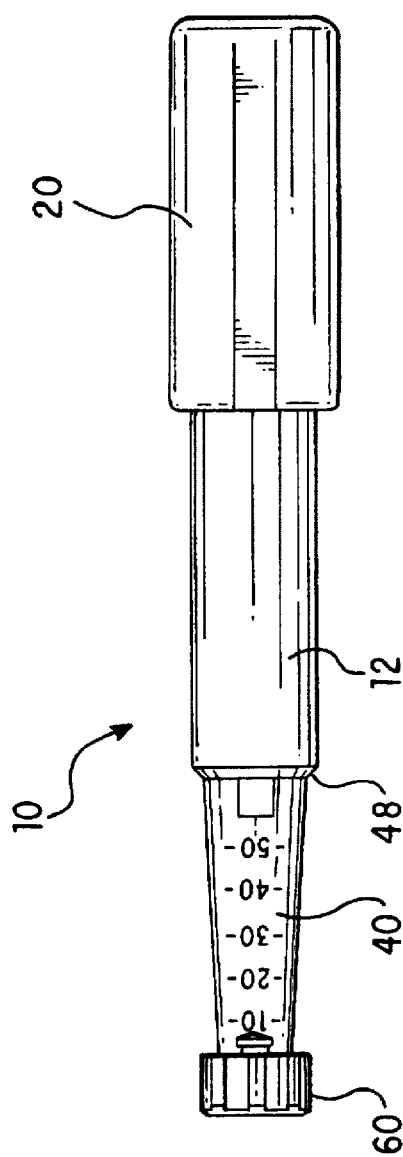
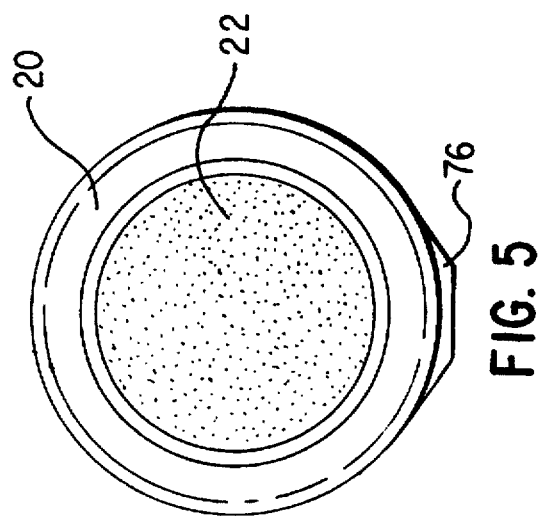
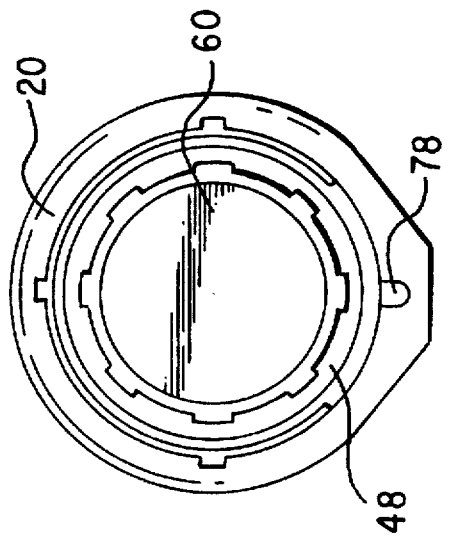

GAS PRESSURED NEEDLE-LESS INJECTION DEVICE AND METHOD

RELATED APPLICATIONS

This is a continuation-in-part of U.S. patent application Ser. No. 08/541,470 filed Oct. 10, 1995 now abandoned.

FIELD OF THE INVENTION

This invention relates to a gas pressured needle-less injection device and method of manufacture, and in particular, embodiments to a single use device.

BACKGROUND OF THE INVENTION

Typically, needle-less medication injections are performed with "permanent gun" instruments, generally referred to as "jet injectors". These devices use either a compression spring or a compressed inert gas to propel the fluid medication (via a push rod plunger) through a small orifice (an injector nozzle) which rests perpendicular to and against the injection site. The fluid medication is generally accelerated at a high rate to a speed of between about 800 feet per second (fps) and 1,200 fps (approximately 244 and 366 meters per second, respectively). This causes the fluid to pierce through the skin surface without the use of a needle, resulting in the medication being deposited in a flower pattern under the skin surface. This method of medication delivery is referred to as a subcutaneous injection.

Conventional jet injectors are cumbersome and awkward to use. Preparing a typical, reusable jet injector for administering an injection requires several steps. For example, prior to each injection, the injector nozzle must be sterilized. The operator removes the delivery nozzle from the jet injector and boils the nozzle in water to assure a reasonable degree of sterilization. After the nozzle is cleaned, the user replaces it on the instrument and prepares the instrument for loading the medication which is to be injected into the skin. A concern often associated with the nozzle in these reusable systems is that, due to a relatively small opening (approximately 0.004" or less), the nozzle has a tendency to clog up if the device is left unused for a period of time or if the user does not clean the instrument each time after being used and prior to its reuse.

In addition, loading known jet injectors with medication is a time consuming and delicate operation. First, an adaptor which contains a needle is placed through the rubber septum of the medication vial. The nozzle of the jet injector is then mated to the needle adaptor in the medication vial. The operator then proceeds to draw up medication into the delivery chamber of the jet injector. This operation may be repeated several times, until the trapped air in the delivery chamber is removed. When this pre-injection operation is complete, the operator selects an injection site and administers the injection.

However, a used and worn delivery orifice can slow down the delivery speed of the injected fluid, which results in inadequate penetration and causes bruising of the skin at the injection site. In addition, the improper use of jet injectors creates bruising (subdermal hematoma) when the nozzle is not firmly pressed against the injection site. Bruising also may occur if the nozzle opening (orifice) is partially clogged or worn out.

Conventional jet injectors are also somewhat dangerous to use, since they can be discharged without being placed against the skin surface. With a fluid delivery speed of about 800 fps or higher, a jet injector could injure a person's eye at a distance of up to 15 feet. It should also be noted that jet injectors which have not been properly sterilized are notorious for creating infections at the injection site. In addition, if a jet injector is not positioned properly against the injection site, the injection can be short of the measured dosage, thereby creating wetting on the skin surface, which leads to additional problems associated with improper dosage amounts.

Moreover, it should also be noted that compression spring propelled jet injectors do not offer linear delivery speeds (constant speed of the fluid being injected). In addition to this problem, spring propelled jet injectors with weak (e.g., deteriorated) springs often slow the fluid delivery speed down while the fluid is being administered into the skin which can result in improper fluid penetration. Reduced speed of the fluid can cause improper dosing and bruising at the injection site (referred to as subdermal hematoma).

SUMMARY OF THE DISCLOSURE

It is an object of an embodiment of the present invention to provide an improved disposable jet injector with simplified operating and safety features, that obviates for practical purposes, the above-mentioned limitations.

According to an embodiment of the present invention, a needle-less injector suitable for injecting liquid medication through a skin surface of a patient include a housing, a driver and a trigger. The housing contains the liquid medication to be injected into the patient. The driver forces the medication out of the housing at a sufficient speed to pierce the skin surface of the patient. The resistance sensitive trigger is coupled to the driver and is used to activate the driver to force the liquid medication out of the housing. The resistance sensitive trigger is activated upon application of a predetermined amount of pressure to the resistance sensitive trigger that is opposed by a predetermined amount of resistance from the skin surface of the patient. The predetermined amount of resistance results from the housing having contact with the skin surface of the patient, and when this predetermined amount of resistance is reached the liquid medication is forced out of the housing by the dryer to pierce the skin surface of the patient.

In further embodiments, the housing of the needle-less injector includes a face that is adapted to align the housing to produce the predetermined amount of resistance to allow for activation of the resistance sensitive trigger. Also, the resistance sensitive trigger is preferably coupled to the housing to permit axial movement of the resistance sensitive trigger along the housing. However, the fit tolerances between the housing and the resistance sensitive trigger are selected to permit activation of the resistance sensitive trigger when the housing is aligned between 0 and 10 degrees off an axis perpendicular to the skin surface of the patient. In addition, the resistance sensitive trigger is preferably positioned to be between the skin surface of the patient and an activating appendage (such as an hand, arm or the like) of a user when activating the driver the force the medication out from the housing.

In particular embodiments, the resistance sensitive trigger includes a resistance element that activates at a lower amount of pressure than the predetermined amount of resistance by the skin surface of the patient. For example, the resistance sensitive trigger includes a cap that is slidably attached to the housing and the resistance element includes a spring coupled between the housing and the cap. Thus, upon application of the predetermined amount of pressure to the cap of the resistance sensitive trigger, the spring compresses when the opposing resistance from the skin surface of the patient reaches the predetermined amount of resistance to activate the driver to force the liquid medication out of the housing to pierce the skin surface of the patient.

According to further embodiments of the present invention, a compressed gas activated needle-less injector device is suitable for injecting liquid medication through the skin surface. The housing of the needle-less injector includes a main body portion, a valve and a chamber housing portion. The main body portion includes a first gas chamber, a passageway and a second gas chamber which is in gaseous communication with the first gas chamber through the passageway. The first gas chamber contains a pre-filled compressed gas, such as inert gas, that exits through the passageway. The second gas chamber partially contains the driver. The pressure of the compressed gas is sufficiently high to accelerate the liquid medication at a speed sufficient to pierce through the skin surface. The valve is detachably mounted to block the passageway to prevent the flow of the compressed gas from the first gas chamber until needed. The valve is positioned in between the first gas chamber and the second gas chamber. The chamber housing portion is securely coupled to the main body portion and includes a liquid chamber and an orifice. In preferred embodiments, the liquid chamber holds the pre-filled and pre-measured liquid medication and is in fluid communication with the driver. The driver can be formed by a piston disposed and movable within the liquid chamber, and a plunger disposed and movable within the liquid chamber along with the piston to force the liquid medication out from the liquid chamber through the orifice. The orifice is formed in one end of the chamber housing portion and is in fluid communication with the liquid chamber. In operation, the compressed gas, when released from the first gas chamber, pushes the liquid forcing assembly, which in turn pushes the liquid medication out through the orifice to pierce the skin surface of the user.

In the embodiment discussed above, the piston has a head which is disposed within the second gas chamber. The head creates an air and fluid tight seal so that the compressed gas released from the first gas chamber is trapped in the second gas chamber.

In a further embodiment, the injector device is equipped with a lever for breaking the valve. In particular embodiments, the lever is slidably mounted through a side wall of the main body adjacent to the valve so that when one end of the lever is pushed in, the other end of the lever breaks off the valve, thus releasing the compressed gas into the second gas chamber. The resistance sensitive trigger may include an incline ramp surface that pushes the lever inward when the resistance sensitive trigger is depressed. In preferred embodiments, a coil spring is positioned between the resistance sensitive trigger and the main body portion to bias the resistance sensitive trigger in an un-depressed state. A retainer, such as a retainer ring, may be used to couple the resistance sensitive trigger to the main body portion, and a protective cover, such as a screw-on cap may be used to cover the orifice to maintain sterility of the injection device.

Other features and advantages of the invention will become apparent from the following detailed description, taken in conjunction with the accompanying drawings which illustrate, by way of example, various features of embodiments of the invention.

BRIEF DESCRIPTION OF THE DRAWINGS

A detailed description of embodiments of the invention will be made with reference to the accompanying drawings, wherein like numerals designate corresponding parts in the several figures.

FIG. 3 is an external side view of an injector device;

FIG. 4 is an external front view of an injector device;

FIG. 5 is an external rear view of an injector device;

DETAILED DESCRIPTION OF THE PREFERRED EMBODIMENTS

Figure 1:
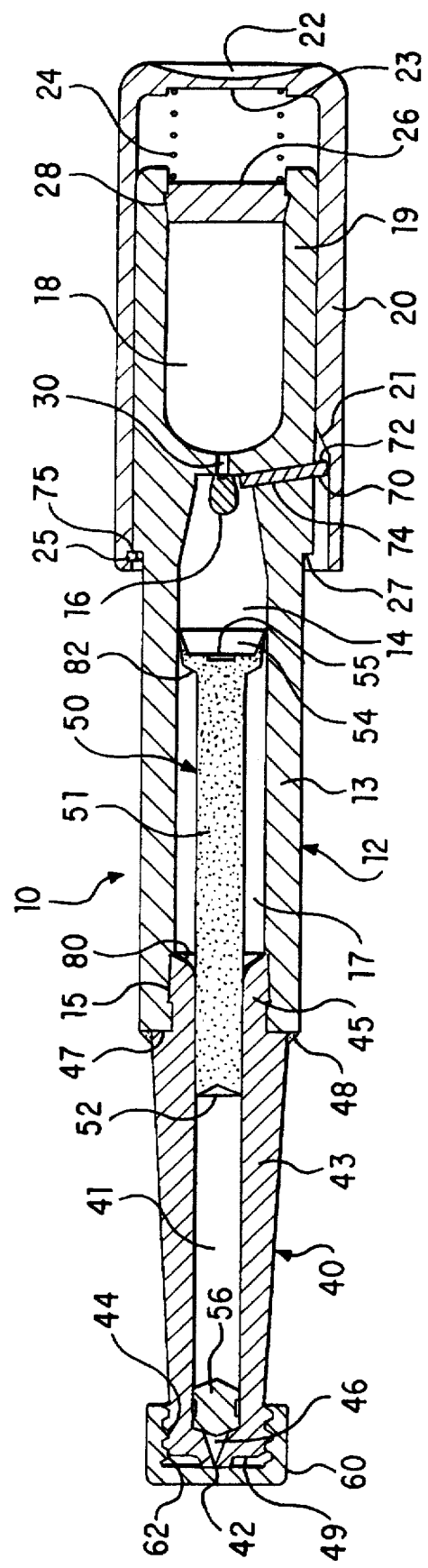
FIG. 1 is a cross-sectional diagram of an injector device according to an embodiment of the invention.

As shown in the drawings for purposes of illustration, the invention is embodied in a needle-less injector. In preferred embodiments of the present invention, the a gas powered needle-lee injector device that is pre-loaded with medication and is adapted for a single use. Preferably, the needle-less injector is for use with human beings. However, it will be recognized that further embodiments of the invention may be used on animals or in other applications requiring needle-less injection, such as passing injectable substances through a porus membrane or the like. In addition, the needle-less injector may uses springs, pyrotechnic charges or the like instead of gas power as the injection delivering force.

As shown in the drawings, a needle-less injection device according to an embodiment of the invention is embodied in a pen sized device. The needle-less injector device 10 according to an embodiment of the invention is useful for hypodermic injection of medication without piercing the skin (non-invasive) with a needle and represents an improvement over known devices. The device 10 may be used as a single dose disposable injector to deliver a dosage of fluid medication. The preferred embodiment ensures precise delivery through an orifice with the diameter of approximately 0.0032" (approximately 0.08 mm). However, larger or smaller diameters may be used, as long as accurate penetration of the skin and delivery of the medication can be maintained. The fluid is linearly accelerated via pneumatic propulsion. Safety is maintained and inadvertent activation of the injection device 10 is avoided via a pressure (e.g., resistance) sensitive triggering feature which allows for proper tensioning of the nozzle and orifice at the injection site prior to automatic medication deployment. For example, activation of the injector device 10 will not occur until the injector is properly positioned to provide the required resistance from the skin surface of the patient to allow for sufficient tension and pressure to be applied to a trigger of the injector device 10 to activate it to deliver the dosage of medication. Improper positioning resulting in insufficient resistance by the skin surface of the patient will prevent the injector device from being inadvertently activated. For example, tight tolerances between a trigger cap and a housing will prevent the cap from sliding along the housing to trigger the device 10, if the device 10 is more than 10 degrees off of an axis perpendicular to the skin surface of the patient.

The device utilizes prepackaging and precisely measured dosages for a variety of medical applications. However, alternative embodiments may be loaded prior to injection. The injector device 10 can be manufactured in various custom sizes for precise medication delivery over a wide range of medication types and dosage amounts. Preferred embodiments allow for a single injection in amounts that range from about 1/20th of one cubic centimeter(cc) to 1.0 cc. The type of injector device 10 is typically used on human patients. However, in alternative embodiments, a larger injector device with larger medication capacity may be constructed and used on animals, such as livestock or the like.

FIG. 1 shows a needle-less injector device 10 according to an embodiment of the invention. The injector device 10 has a main body 12, a chamber housing 40, a cap 60, a piston 50, an actuating member 20, and a first gas chamber 18. The main body 12 includes a first body portion 13 integrally connected to a second body portion 19 (main body 12, first body portion 13, and second body portion 19 may be a single unit in design and manufacturing). In the preferred embodiment of the device, the second body portion 19 has a slightly larger diameter than that of the first body portion 13. A flange 27 is formed due to a larger diameter of the second body portion 19. The first body portion 13 and the second body portion 19 each has an elongated cylindrical shape. However, in alternative embodiments, other shapes such as rectangular, triangular or the like may be used. The main body 12 also has an elongated cavity 17 centrally disposed along the length of the first body portion 13 and partially along the length of the second body portion 19. The elongated cavity 17 forms an opening which is located on the end of the main body 12, opposite of the second body portion 19. The elongated cavity 17 has a cylindrical shape with substantially the same diameter. However, in alternative embodiments, other shapes such as rectangular, triangular or the like may be used. The diameter of the elongated cavity 17 gradually tapers off as the elongated cavity 17 nears the second body portion 19. The smaller diameter portions of the elongated cavity 17 limits the backward movement of the piston 50 and tends to increase the rate of acceleration when the jet injection device 10 is first activated.

The second body portion 19 includes a lever passageway 74 and the first gas chamber 18 for storing compressed inert gas, such as carbon dioxide. However, alternative embodiments may use other gases or a gas/liquid combination. The elongated cavity 17 (i.e., containing a second gas chamber 14) and the first gas chamber 18 are coupled together to provide gaseous communication with each other through a passageway 30. The first gas chamber 18 of the second body portion 19 has an opening on the opposite end of the passageway 30, through which compressed gas is pre-filled into the first gas chamber 18. A retention groove 28 (preferably ring shaped) is formed around the inner diameter of the first gas chamber 18 near the end of the large opening in the first gas chamber. A chamber plug 26 is disposed within the opening of the first gas chamber 18 to seal in the compressed inert gas, once the gas has been loaded. The chamber plug 26 forms an air tight seal in the first gas chamber 18 by engaging the retention groove 28. The retention groove 28 also prevents the chamber plug 26 from detaching itself from the second body portion 19 due to the presence of compressed gas in the first gas chamber 18. The chamber plug 26 is configured and sized to firmly fit into the opening of the first gas chamber 18. In alternative embodiments, instead of the retention groove 28, the inner surface of the first gas chamber may be threaded so that the chamber plug 26 (with corresponding outer threads) may be screwed into the first gas chamber 18. Alternatively, the first gas chamber 18 may be a sealed compartment in which compressed gas is injected through a valve. A seal may be obtained by using an adhesive or other suitable materials. The chamber plug 26 may be made of any suitable rigid materials, such as plastic, rubber, ceramic, metal, composites and the like. Although the main body 12 may be made of plastic by, such process as an injection molding, other suitable materials, such as ceramic, glass, metal, composites or the like, may be used. In addition, the first body portion 13 and the second body portion 19 may be formed together as one injection mold or may be formed from separate portions coupled together by adhesives, welding, snap fits or the like. In preferred embodiments, the chamber plug 26 would be plastic welded, glued or otherwise secured in the first gas chamber 18 immediately after the first gas chamber is filled with gas.

Inside the elongated cavity 17, a release tab 16 (or valve) is attached to the wall to block off and seal the passageway 30. In its normal position, the release tab 16 blocks the gas flow from the first gas chamber 18 into the elongated cavity 17. When the release tab 16 is detached or broken off from its original position, the compressed gas from the first gas chamber 18 is released into the elongated cavity 17. More specifically, the compressed gas is released into a second gas chamber 14, which is a part of the elongated cavity 17. The release tab 16 is preferably sufficiently large to fully cover the opening in the passageway 30, thus preventing any gas leak. In the preferred embodiment, the release tab 16 may be molded with the main body 12. Alternatively, the release tab 16 may be attached to the wall by any suitable process, such as using an adhesive, welding or the like. The release tab 16 is preferably detached or broken off by applying force on its side, but it should be attached firmly enough to withstand the pressure exerted by the compressed air in the first gas chamber 18 or a shock from a drop. In addition, the release tab 16 should resist being sheared off until the injector device 10 is placed in contact with the skin of a patient and sufficient resistance is encountered to permit the injector device 10 to be activated by applying sufficient pressure to shear off the release tab 16.

The lever passageway 74 is typically formed on the side wall of the main body 12 and extends from the outer to the inner surface of the second body portion 19 at a slightly slanted angle. However, other configurations may be used. The lever passageway 74 is adapted and configured to hold a lever 70 which protrudes through the lever passageway 74. In the preferred embodiment, the lever 70 is a cylindrical rod with a rounded end 72. The rounded end 72 protrudes out of the second body portion 19. The lever 70 has preferably the sufficiently same cross-section and diameter as the lever passageway 74 to firmly fit inside the passageway 74 to provide a sufficiently tight air and fluid seal to not hinder with the effective performance of the injection device 10. However, there may be some clearance between the lever 70 and the passageway 74 to bleed-out excess gas pressure over a time period once the injector device 10 has been used. In an alternative embodiment, there may be a plurality of levers 70 disposed through a plurality of lever passageways 74 to ensure the removal of a release tab 16. For example, the main body 12 may accommodate two levers at a 90 degree angle to each other so that the combined force of those levers ensure proper detachment of the release tab 16. In addition, the lever 70 and the passageway 74 may be formed of a rectangular rod shape or other suitable shapes. The lever 70 may be made of resilient plastic or other suitable materials.

The chamber housing 40 includes an elongated tubular body 43, a neck portion 45 and a liquid chamber 41 for storing and holding, for example, liquid medication (not shown). The chamber housing 40 has an orifice 42 (or nozzle) at one end and has an opening configured to receive the piston 50 at the other end. The orifice 42 is centrally positioned on an injector face 49. The injector face 49 has a flat surface, except that the center region around the orifice 42 is raised slightly. The raised surface around the orifice 42 provides firm contact against a receiving surface, such as the skin surface (not shown). This helps to insure that the injector is properly positioned and will not be activated until sufficient pressure is applied to the injector device 10.

The outer diameter of the neck portion 45 is smaller than the outer diameter of the elongated tubular body 43 which forms a shoulder portion 47 where the two parts join together. The shoulder portion 47 rests on the surface of the opening formed by the elongated cavity 17 of the main body 12. However, the outer diameter of the neck portion 45 is substantially the same as the inner diameter of the elongated cavity 17 of the main body 12 so that the neck portion 45 firmly fits inside the elongated cavity 17. To firmly engage the neck portion 45 of the chamber housing 40 with the elongated cavity 17 of the main body, the middle section of the neck portion 45 may have a slightly larger outer diameter that fits into a groove 15 formed inside the elongated cavity 17. Once coupled together, the chamber housing 40 cannot be released from the main body 12, unless extreme force is applied. In alternative embodiments, the raised outer diameter of the neck portion is altered to form threads on the outer diameter of the neck portion 45 and matching threads are formed inside the elongated cavity 17 to screw-in the chamber housing 40. This provides the advantage of being able to assemble the device 10 when needed or just prior to giving an injection. This assembly option allows the user to select a variety of different medications or dosages while minimizing the number of complete injectors 10 that must be carried or stocked. It would also facilitate manufacture of the device 10 since the injector 10 and the chamber housing 40 may be manufactured at different times. Further, the main body 12 and the chamber housing 40 may be attached and sealed together by any suitable method, such as adhesives, welding or the like. A ring joint 48, in the form of a plastic weld fillet, is also used to further reinforce the attachment of the chamber housing 40 to the main body 12. In the preferred embodiment, the ring joint 48 abuts against the shoulder portion 47 and the opening surface of the elongated cavity 17. The ring joint 48 provides additional strength to securely hold the chamber housing 40 in the main body 12. Although not shown in the drawings, an O-ring may be placed between the shoulder portion 47 of the chamber housing 40 and the opening surface of the elongated cavity 17 to provide an additional air and fluid tight seal.

For easy measuring and observation of the amount of medication in the liquid chamber 41, the elongated tubular body 43 includes graduations so that the user can determine the amount of medication contained in the injector device 10. The chamber housing 40 can be formed of glass or other suitable materials, such as plastic, ceramic, polycarbonate or the like. In the preferred embodiment, the chamber housing 40 is transparent so that the liquid medication and the various moving parts in the liquid chamber 41 can be visually examined. Also, the chamber housing 40 is disposable, however the chamber housing may be recycled, if desired.

A cap 60 may be mounted on the end of the chamber housing 40 to cover the orifice 42. The cap 60 provides and maintains sterility of the injection device 10 and prevents an accidental discharge of the liquid medication disposed inside the liquid chamber 41 from shock, evaporation or seepage. Threads 44 for mounting the cap 60 are on the outer surface of the end portion of the chamber housing 40. The cap 60 has matching threads 62 on the inner surface so that the cap 60 can be screwed-on at the end portion of the chamber housing 40. Once screwed-on, the cap 60 provides an air and fluid tight seal around the orifice to prevent any foreign material from being introduced into the liquid chamber 41. In alternative embodiments, the cap 60 and the end portion of the chamber housing 40 can be configured so that the cap 60 is snapped-on instead of screwed-on. The cap 60 may be made of any suitably rigid material, such as plastic polymers, rubber, ceramic or the like.

The piston 50 has an elongated cylindrical body 51 with an indented front surface 52 at one end and a head 54 at the opposite end. The head 54 includes a rear surface 55, which is preferably concave. In alternative embodiments, the front and rear surfaces may be flat, or have other suitable shapes. The elongated cylindrical body 51 of the piston 50 is disposed inside the liquid chamber 41 for sliding movement along its length. In preferred embodiments the elongated cylindrical body 51 has substantially the same outer diameter as the diameter of the liquid chamber 41 to provide free sliding movement along the length of the liquid chamber 41. Due to an air and fluid tight seal around a plunger 56, the air and fluid tight seal around the piston 50 may not be necessary. The head 54 of the piston 50 has substantially the same outer diameter as the inner diameter of the elongated cavity 17 to form an air and fluid tight seal with a minimal friction between the head 54 and the walls of the elongated cavity 17. The space defined between the head 54 and the back wall of the elongated cavity 17 is the second gas chamber 14. The head 54 is disposed inside the elongated cavity 17 so that the compressed gas introduced in the second gas chamber 14 expands the head 54 against the wall surface of elongated cavity 17, providing an additional seal, so that the compressed gas introduced into the second gas chamber 14 pushes the piston 50 forward.

Where the lower portion 82 of the head 54 makes contact with the neck portion 45 of the chamber housing 40, the shapes of both portions may be configured to match each other. In the preferred embodiment, the end surface 80 of the neck portion 45 forms a concave surface while the lower portion 82 of the head 54 forms a convex surface. The matching shapes assist in delivering substantially all of the medication to the injection site. However, in alternative embodiments, other suitable shapes, such as a flat surface, may be used, and the piston 50 may be made of any suitable material such as plastic, glass, ceramic, metal, composites or the like.

Also disposed inside the liquid chamber 41 is a plunger 56. The plunger 56 has an outer diameter which is substantially the same as the inner diameter of the liquid chamber 41 to form an air and fluid tight seal. The plunger 56 is disposed between the piston 50 and the orifice 42. The medication is situated in front of the plunger 56 (i.e., between the orifice 42 and the plunger 56) so that the forward movement of the plunger 56 forces the liquid medication toward the orifice 42. The front surface of the plunger 56 may be configured to match the opening defined by an orifice guide 46. In preferred embodiments, the front surface of the plunger 56 has a convex surface to match the concave shape of the orifice guide 46, whose vertex is the orifice 42. The shape of the orifice guide 46 focuses and increases the speed of liquid medication as it exits the orifice 42. The matching shapes of the orifice guide 46 and the plunger 56 tend to minimize the waste of medication, since most of the medication is forced out through the orifice 42. The shape of the rear surface of the plunger 56 matches the front surface 52 of the piston 50. The similarly shaped configuration provides for an even distribution of the pressure on the rear of the plunger 56 when the piston 50 moves forward. This tends to minimize jams or distortion as the plunger 56 is driven forward. The plunger 56 is generally made of rubber or other suitable materials, such as plastic, composites or the like. In alternative embodiments, the plunger 56 and the piston 50 formed as and integrated piece either by attaching the plunger 56 to the piston 50 or by molding the piston assembly to include the plunger 56.

A resistance sensitive trigger includes an actuating member 20 that is an elongated tubular member that slides over the second body portion 19 of the main body 12. The actuating member 20 has a trigger portion 22, a raised rail 76 (see FIG. 2), and a retainer slot 25. The actuating member 20 is enclosed at one end and has an opening at the other end. On the inner surface of the enclosed end, there is a spring surface 23 for holding or mounting a coil spring 24. The resistance sensitive trigger also includes a coil spring 24 that is positioned between a spring surface 23 and the chamber plug 26 and provides a resilient bias toward the rear end. The proper use of the injection device 10 requires that the injector device 10 be positioned substantially perpendicular to the skin surface before the medication is injected into the injection site. Therefore, the tension strength of the coil spring 24 should be sufficiently strong to prevent accidental triggering when the injection device 10 is not properly positioned. Typically, a minimum applied pressure of 2.2 lbs/in$^2$ (1.0 kg/2.5 cm$^2$) is required to discharge the injector. However, slight lower or higher minimums may be required depending on the skin of the patient or where the injection is to be administered. In alternative embodiments, alternate resistance elements may be used instead of the coil spring 24, such as deformable rubber or plastic, strain gauges or the like.

In the front opening of the actuating member 20, there is a retainer slot 25 for mounting a retainer 75. The retainer slot 25 is formed around the inner circumference of the actuating member 20, extending from one side of the raised rail 76 to the other side. The retainer 75, which is in a form of a thin circular rod, is mounted into the retainer slot 25. The circumferential length of the retainer 75 is substantially equal to that of the retainer slot 25. When the actuating member 20 is installed onto the second body portion 19, the retainer 75 generally rests against the flange 27. This prevents the actuating member 20 from detaching itself from the second body portion 19 due to rearward force exerted by the coil spring 24. The retainer 75 may be made of plastic or other suitable materials such as metal or the like. In alternative embodiments, the retainer 75 and the actuating member 20 may be formed as one integral member by molding process or other suitable processes. The actuating member 20 is typically made of plastic or other suitably rigid and resilient materials, such as glass, composite, ceramic or metal. The trigger portion 22 is on the outer end surface of the actuating member 20. It preferably forms a concave surface and is coated with a textured material to prevent depressing force, such as from a thumb, from slipping.

Figure 2:
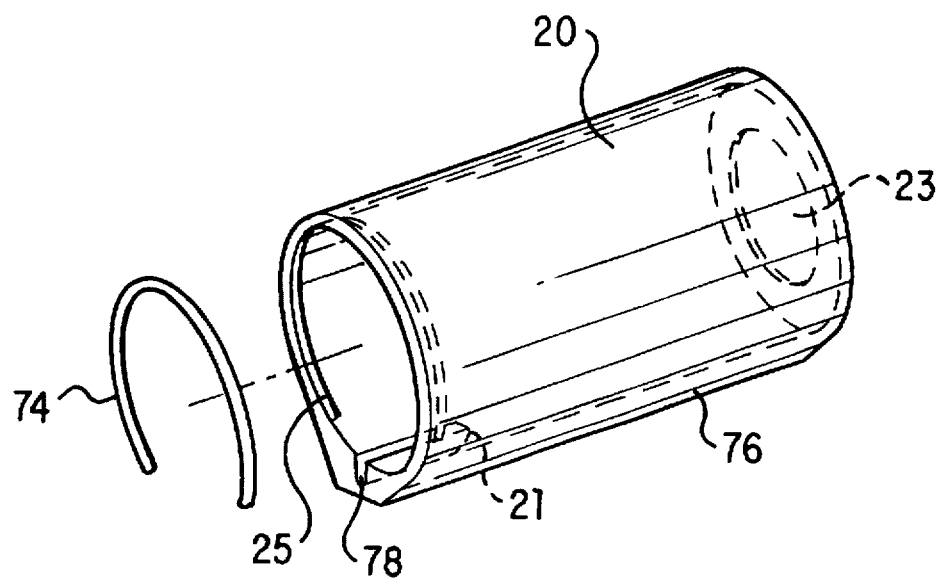
FIG. 2 is an exploded view of an actuating member according to an embodiment of the invention.

FIG. 2 shows an exploded view of the actuating member 20 of the resistance sensitive trigger. As shown in FIG. 2, the raised rail 76 extends along the length of the outer surface of the actuating member 20. A conduit 78 is formed along the length of the raised rail 76. The cross-sectional shape and dimension of the conduit is configured to accommodate the protruding portion of the lever 70. The raised rail 76 has a thickness which varies along its length. The thickness of the raised rail 76 is thinner near the opening of the actuating member 20. Toward the rear portion of the actuating member 20 where a lever 70 is situated, a gradually inclined region 21 is formed on the inner surface of the raised rail 76.

When the actuating member 20 is not depressed, the lever 70 rests on the flat thinner inner surface of the raised rail 76. This is the normal state of the injection device 10 prior to injection. When the actuating member 20 is depressed, the actuating member 20 moves forward, and the inclined region 21 forces the lever 70 toward the center of the second body portion 19. The inward movement of the lever tears (or breaks off) the release tab 16 and consequently releases the compressed gas in the first gas chamber 18. The raised rail 76 can be formed as integral part of the actuating member by a molding process or other suitable processes.

The operation of the needle-less injector device according to the preferred embodiment will now be discussed. Initially at the manufacturing facility, the injection device is pre-filled with medication in the liquid chamber 41 and is pre-filled with compressed gas in the first gas chamber 18. The user (or an operator) unscrews (or unsnaps) the cap 60 from the main body 12, thus revealing the orifice 42 of the injector device 10. The user then positions the injector device 10 perpendicularly against the skin surface to provide firm and secure contact of the orifice 42 against the skin surface. The injector device 10 requires the device 10 to be properly oriented and in contact with the skin of the patient, since the injector device 10 is designed so that it cannot be activated or discharged without the device 10 being placed against the skin surface. Otherwise, with a fluid delivery speed of about 800 fps or higher, a jet injector could injure a person's eye or other part of the body. In addition, if the jet injector were not positioned properly against the injection site, and the injection device were activated, the dosage can be short of the measured dosage, thereby creating wetting on the skin surface, which leads to additional problems associated with improper dosage amounts.

As the trigger portion 22 of the actuating member 20 is depressed, the skin surface of the patient resists the pressure being applied to the actuating member 20 of the resistance senitive trigger and the coil spring 24 is compressed between the chamber plug 26 and the spring surface 23. Sufficient pressure (generally a minimum of 2.2 lbs/m$^2$ (1.0 kg/2.5 cm$^2$)) must be applied at the trigger portion 22 to overcome the tension of the coil spring 24. Concurrently, as the inclined region 21 pushes against the lever 70, the lever 70 is pushed inward toward the center axis of the main body 12. As the actuating member 20 is pressed further against the skin surface, the lever 70 pushes against the side of the release tab 16, tearing (or breaking off) the release tab 16. This exposes the opening of the passageway 30, and the compressed gas stored in the first gas chamber 18 is released into second gas chamber 14. When sufficient pressure is built up inside the second gas chamber 14, the piston 50 is pushed forward so that it slides forward in the liquid chamber 41. The seal around the head 54 of the piston 50 substantially prevents any gas from leaking into the other parts of the elongated cavity. The forward movement of the piston 50 causes the front surface 52 of the piston 50 to make contact with the rear surface of the plunger 56, to move the plunger 56 forward. As the plunger 56 moves forward, the liquid medication exits from the orifice 42 at a high speed and penetrates the skin surface at the injection site.

FIGS. 3 through 5 show external views of a side, a front and a rear of the injector device 10, respectively. As shown in these figures, the injection device 10 according to an embodiment of invention is compact and therefore easy to carry. Also, the graduations shown on the surface of the chamber housing 40 in FIG. 3 provides an indication of how much medication is stored in the injector device 10.

Figure 6:
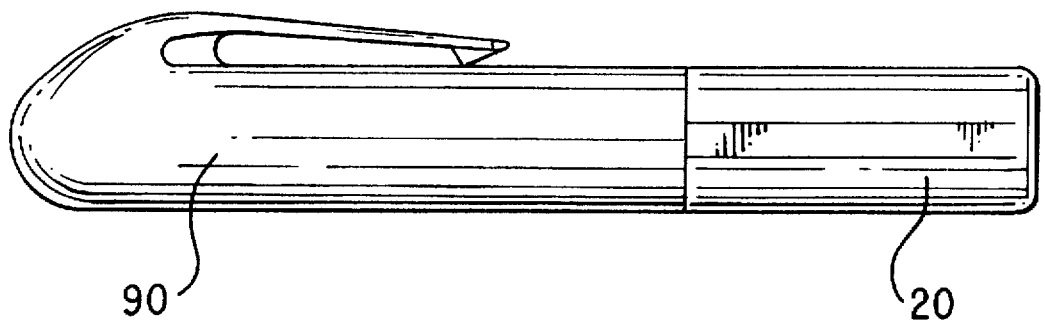
FIG. 6 is an external view of an injector device with a safety cap.

FIG. 6 shows an external view of the injector device 10 with a safety cap 90. The safety cap 90 provides accidental discharge of the injector device 10 by preventing the forward movement of the actuating member 20. The safety cap 90 may be equipped with a pocket clip so that the injector device 10 can be conveniently transported in a shirt pocket. When the safety cap 90 is initially installed on the injector device 10, a seal, such as a plastic hot gun seal or the like, may be placed at multiple points around the joint formed by the safety cap 90 and the actuating member 20. The seal evidences any tempering of the injector device 10. The safety cap 90 may be made of similar materials as used in other parts of the injector device 10, such as plastic, fiberglass, polycarbonate, or the like.

While the description above refers to particular embodiments of the present invention, it will be understood that many modifications may be made without departing from the spirit thereof. The accompanying claims are intended to cover such modifications as would fall within the true scope and spirit of the present invention.

The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed is:

1. A pre-filled compressed gas activated needle-less injector device suitable for injecting pre-filled liquid medication through the skin surface, the device comprising:
   a main body having a first gas chamber, a second gas chamber and a passageway in gaseous communication with the first and the second chambers, wherein the first gas chamber contains a pre-filled compressed gas that exits through the passageway and into the second chamber;
   a valve detachably mounted to block the passageway to prevent the flow of the compressed gas from the first gas chamber into the second chamber until detached;
   a chamber housing coupled to the main body, the chamber housing comprising:
      a liquid chamber that holds the liquid medication;
      a liquid forcing assembly disposed within the liquid chamber that forces the liquid medication out from the liquid chamber; and
      an orifice formed in one end of the chamber housing and in fluid communication with the liquid chamber, wherein when the valve is permanently detached from blocking the passageway, the compressed gas is released from the first gas chamber into the second gas chamber and the compressed gas pushes the liquid forcing assembly which in turn pushes the liquid medication exits through the orifice and pierces the skin surface; and
   an actuating member mounted on the main body to permanently detach the valve to release the compressed gas when a predetermined pressure is applied to the actuating member.

2. A needle-less injector device according to claim 1, further including a coil spring positioned between the actuating member and the main body to bias the actuating member in an un-depressed state, wherein the coil spring has sufficient tension so that the predetermined pressure to activate the actuating member is established when the orifice is positioned substantially perpendicular to the skin surface.

3. A needle-less injector device according to claim 1, further including a lever slidably mounted through a side wall of the main body adjacent to the valve and triggered by the actuating member so that when one end of the lever is pushed in, the other end of the lever permanently detaches the valve from blocking the passageway thus releasing the compressed gas into the second gas chamber.

4. A one-time use, pre-filled compressed gas activated needle-less injector device suitable for injecting pre-filled liquid medication through the skin surface, the device comprising:
   a main body having a first gas chamber, a second gas chamber and a passageway in gaseous communication with the first and the second chambers, wherein the first gas chamber contains a pre-filled compressed gas that exits through the passageway and into the second chamber;
   a valve detachably mounted to block the passageway to prevent the flow of the compressed gas from the first gas chamber into the second chamber until detached;
   a chamber housing coupled to the main body, the chamber housing comprising:
      a liquid chamber that holds the liquid medication;
      a piston disposed and movable within the liquid chamber, wherein the piston includes a head disposed within the main body and creates an air and fluid tight seal so that compressed gas released from the first gas chamber is trapped in the second gas chamber;
      a plunger disposed and movable within the liquid chamber along with the piston to force the liquid medication out from the liquid chamber; and
      an orifice formed in one end of the chamber housing and in fluid communication with the liquid chamber, wherein when the valve is permanently detached from blocking the passageway, the compressed gas is released from the first gas chamber into the second chamber and the compressed gas pushes the piston which in turn pushes the plunger with the piston so that the liquid medication exits through the orifice and pierces the skin surface;
   an actuating member mounted on the main body to permanently detach the valve to release the compressed gas when a predetermined pressure is applied to the actuating member;
   a coil spring positioned between the actuating member and the main body to bias the actuating member in an un-depressed state, wherein the coil spring has sufficient tension so that the predetermined pressure to activate the actuating member is established when the orifice is positioned substantially perpendicular to the skin surface; and
   a lever slidably mounted through a side wall of the main body adjacent to the valve and triggered by the actuating member so that when one end of the lever is pushed in, the other end of the lever permanently detaches the valve from blocking the passageway thus releasing the compressed gas into the second gas chamber.

5. A method for constructing a pre-filled compressed gas activated needle-less injector device suitable for injecting pre-filled liquid medication through the skin surface, the method comprising the steps of:
   forming a main body having a first gas chamber, a second gas chamber and a passageway in gaseous communication with the first and the second chambers, wherein gases in the first gas chamber exit through the passageway and into the second chamber;
   detachably mounting a valve to block the passageway to prevent the flow of the compressed gas from the first gas chamber into the second chamber until detached;

forming a chamber housing by the steps of:
- forming a liquid chamber that holds the liquid medication,
- forming a liquid forcing assembly disposed within the liquid chamber that forces the liquid medication out from the liquid chamber, and
- forming an orifice formed in one end of the chamber housing and in fluid communication with the liquid chamber, wherein when the valve is permanently detached from blocking the passageway the compressed gas is released from the first gas chamber and the compressed gas pushes the liquid forcing assembly which in turn pushes the liquid medication out through the orifice and through the skin surface;

coupling the chamber housing to the main body;

mounting an actuating member on the main body to permanently detach the valve to release the compressed gas when a predetermined pressure is applied to the actuating member;

disposing a coil spring between the actuating member and the main body to bias the actuating member away from the main body, wherein the coil spring has a sufficient tension so that the predetermined pressure is established to activate the actuating member when the orifice is positioned substantially perpendicular to the skin surface;

filling the first gas chamber with compressed gas;

filling the liquid chamber with liquid medication; and slidably mounting a lever through a side wall of the main body adjacent to the valve so that when one end of the lever is pushed in by the actuating member, the other end of the lever permanently detaches the valve from blocking the passageway thus releasing the compressed gas into the second gas chamber.

6. A method according to claim 5 wherein the step of forming the liquid forcing assembly includes the steps of:

installing a piston movable within the liquid chamber, wherein the piston includes a head disposed within the main body and creates an air and fluid tight seal to define the second gas chamber so that compressed gas released from the first gas chamber is trapped in the second gas chamber; and installing a plunger movable within the liquid chamber along with the piston to force the liquid medication out from the liquid chamber.

* * * * *